(12) United States Patent
Dolatkhani et al.

(10) Patent No.: US 9,708,480 B2
(45) Date of Patent: Jul. 18, 2017

(54) METASTABLE POLYMER COMPOSITIONS FOR OPHTHALMIC IMPLANT INJECTION DEVICES

(71) Applicant: POLYMEREXPERT SA, Pessac (FR)

(72) Inventors: Marc Dolatkhani, Cestas (FR); Christophe Hupin, Salles (FR)

(73) Assignee: POLYMEREXPERT SA, Pessac (FR)

( * ) Notice: Subject to any disclaimer, the term of this patent is extended or adjusted under 35 U.S.C. 154(b) by 0 days.

(21) Appl. No.: 14/377,428

(22) PCT Filed: Feb. 7, 2013

(86) PCT No.: PCT/FR2013/050258
§ 371 (c)(1),
(2) Date: Aug. 7, 2014

(87) PCT Pub. No.: WO2013/117863
PCT Pub. Date: Aug. 15, 2013

(65) Prior Publication Data
US 2016/0015865 A1 Jan. 21, 2016

Related U.S. Application Data

(60) Provisional application No. 61/647,751, filed on May 16, 2012.

(30) Foreign Application Priority Data
Feb. 7, 2012 (FR) ...................................... 12 51146

(51) Int. Cl.
| | | |
|---|---|---|
| *A61L 31/04* | (2006.01) |
| *C08L 53/00* | (2006.01) |
| *C08L 23/12* | (2006.01) |
| *C08L 33/04* | (2006.01) |
| *C08L 39/06* | (2006.01) |
| *C08G 18/10* | (2006.01) |
| *C08L 77/12* | (2006.01) |
| *C08G 18/48* | (2006.01) |
| *C08G 18/67* | (2006.01) |
| *C08G 18/75* | (2006.01) |
| *C08G 18/40* | (2006.01) |
| *C08G 18/42* | (2006.01) |
| *C08L 75/16* | (2006.01) |
| *C08L 23/10* | (2006.01) |
| *C08G 18/22* | (2006.01) |
| *C08G 18/28* | (2006.01) |
| *A61F 2/16* | (2006.01) |

(52) U.S. Cl.
CPC ............ *C08L 23/12* (2013.01); *A61L 31/041* (2013.01); *C08G 18/10* (2013.01); *C08G 18/227* (2013.01); *C08G 18/283* (2013.01); *C08G 18/4018* (2013.01); *C08G 18/4277* (2013.01); *C08G 18/4841* (2013.01); *C08G 18/6705* (2013.01); *C08G 18/758* (2013.01); *C08L 23/10* (2013.01); *C08L 33/04* (2013.01); *C08L 39/06* (2013.01); *C08L 75/16* (2013.01); *C08L 77/12* (2013.01); *A61F 2/16* (2013.01); *A61F 2/1662* (2013.01)

(58) Field of Classification Search
None
See application file for complete search history.

(56) References Cited

U.S. PATENT DOCUMENTS

| 5,716,364 | A | 2/1998 | Makker | |
|---|---|---|---|---|
| 6,083,230 | A | 7/2000 | Makker | |
| 6,283,975 | B1 | 9/2001 | Glick | |
| 6,398,788 | B1 | 6/2002 | Makker | |
| 2002/0133167 | A1 | 9/2002 | Harish | |
| 2002/0156141 | A1* | 10/2002 | Kelly | ................. C08G 18/4072 521/155 |
| 2003/0195522 | A1 | 10/2003 | McNicholas | |
| 2004/0133212 | A1 | 7/2004 | Makker | |
| 2005/0221041 | A1 | 10/2005 | Makker | |
| 2005/0288510 | A1* | 12/2005 | Mader | .................. C08K 5/0083 546/186 |
| 2008/0293886 | A1* | 11/2008 | Karl | ........................ C08L 53/00 525/89 |
| 2009/0281516 | A1* | 11/2009 | Ahern | .................... B01L 3/5082 604/415 |
| 2010/0100070 | A1* | 4/2010 | Shimizu | .................... A61J 1/10 604/410 |
| 2010/0105717 | A1* | 4/2010 | Gordon | ................ A61K 9/1617 514/291 |

FOREIGN PATENT DOCUMENTS

| JP | 56-090838 | 7/1981 |
|---|---|---|
| JP | 05-201965 | 8/1993 |
| WO | 96/22062 A1 | 7/1996 |
| WO | 98/01089 A1 | 1/1998 |
| WO | 98/26733 A1 | 6/1998 |
| WO | 00/62713 A1 | 10/2000 |
| WO | 01/10352 A1 | 2/2001 |
| WO | 2005/018505 A1 | 3/2005 |
| WO | 2006/128795 A2 | 12/2006 |
| WO | 2007/021412 A2 | 2/2007 |
| WO | 2007/030009 A2 | 3/2007 |
| WO | 2007/054644 A2 | 5/2007 |
| WO | 2009/156628 A2 | 12/2009 |
| WO | 2010/028873 A1 | 3/2010 |
| WO | 2010/059655 A1 | 5/2010 |
| WO | 2010/118080 A1 | 10/2010 |

OTHER PUBLICATIONS

Ilhan Ozen, et al :"Modification of Surface Properties of Polypropylene Films by Blending Poly(ethylene-b-ethylene oxide) and its Application" Polymer Bulletin, Springer, Berlin, DE vol. 68, No. 2, Oct. 21, 2011 (Oct. 21, 2011), pp. 575-595, XP019988683; ISSN: 1436-2449.

* cited by examiner

*Primary Examiner* — Jeffrey Mullis
(74) *Attorney, Agent, or Firm* — Lucas & Mercanti, LLP

(57) ABSTRACT

The invention relates to metastable polymer compositions, use thereof for manufacturing medical devices or medical device components having a slippery surface as well as the devices with slippery surfaces resulting from these metastable polymer compositions, in particular in the field of ophthalmic injectors.

14 Claims, No Drawings

METASTABLE POLYMER COMPOSITIONS FOR OPHTHALMIC IMPLANT INJECTION DEVICES

CROSS-REFERENCE TO RELATED APPLICATIONS

This application is a 371 of PCT/ES2012/070139 filed Mar. 6, 2012, which in turn claims the priority of PCT/ES2011/070692 filed Oct. 5, 2011, the priority of both applications is hereby claimed.

The invention relates to novel polymer compositions in a metastable morphological state capable of leading directly after utilization to biomedical devices possessing slippery surface properties. The invention relates to said metastable polymer compositions, their use for manufacturing devices or device components having a slippery surface, the slippery-surface devices resulting from these metastable polymer compositions and their uses, in particular in the field of ophthalmic injectors.

Replacement of the lens of the eye affected by cataract is ensured by intraocular implants. Surgery using phacoemulsification allows the destruction of the natural lens and its removal through a small incision. Implants made of flexible and pliable materials have been developed, which can be inserted using injection devices through the micro-incision made for the phacoemulsification.

The injection system is composed of a tubular body in which the injection plunger slides surmounted by a cartridge for loading the ophthalmic implant and by a cone-shaped tip the diameter of which reduces towards the injection end. There are two types of injection system:
  the single-part injector in which the cartridge for loading the implant and the tip are connected to the tubular body of the injector.
  the injector constituted by two parts, in which the cartridge for loading the implant and the tip are separate from the tubular body. The two parts fit together after the implant is loaded into the cartridge.

Whichever type of injector is adopted, the surgeon presses on the plunger, the end of which pushes the implant which is located in the cartridge; the latter is forced further into the tip of the injector and finally comes out of the injector completely folded. It is thus possible to inject an implant with a diameter greater than 6 mm through an incision smaller than 3 mm. Very great stresses are then exerted on the implant during the transfer. In order to limit the injection force and allow the implant to come out of the tip without being damaged, it is necessary, on the one hand, to optimize the geometry of the injector and, on the other hand, to use a "lubricant".

The patent applications EP 1 173 115, EP 2 344 073 or WO2007/054644 and WO2007/021412, describe injection systems with different geometric designs; numerous injectors making use of the different forms described in these patent applications are commercially available.

The mechanical characteristics of the material constituting the tip also have an influence on the injectability. In fact, the thermoplastic material used for manufacturing the tip must allow a certain deformability to accompany the stresses to which the implant is subjected, whilst exhibiting good rigidity. Furthermore, it must be possible to use the thermoplastic materials at high rates. These materials are preferably chosen from the family of the polyolefins and more particularly polypropylene, the polyamides, polyurethanes and polyesters.

However, the choice of the material constituting the tip and the cartridge as well as the optimization of its geometry are not sufficient for implants to be satisfactorily injected via micro-incisions. It is imperative to use a lubricant allowing the implant to slide in the tip and the cartridge. The approaches allowing lubrication, described in the literature, are the use of a blooming agent and the utilization of a coating.

The first route relates to the use of a blooming agent incorporated in the thermoplastic polymer by mixing (or to use the conventional term, "compounding"). This is generally an oleophilic or surfactant organic molecule of low molar mass, containing 10 to 30 carbon atoms per molecule, derived from carboxylic acid and of the glycerol monostearate (GMS), glycerol monopalmitate or glycerol monooleate type etc. Mixed with polypropylene or polyamide, this type of molecule spreads uniformly throughout the thermoplastic support obtained by injection and finally migrates to the surface of the support after several days or even several weeks. This blooming phenomenon is linked to the small size of the surfactant molecule which is mobile compared with the macromolecular chains of the thermoplastic material. By way of example, patents U.S. Pat. No. 6,733,507, U.S. Pat. No. 6,679,891 and U.S. Pat. No. 6,083,230 describe polypropylene (PP) cartridges containing a lubricating agent which migrates to the surface by a "blooming" phenomenon. The injection of the implant is carried out after the addition of a viscous product (aqueous solution of hyaluronate or hydroxypropylmethyl cellulose).

This approach has two major drawbacks.

The first is the presence of white traces on the injected implants. These are due to the fact that the blooming agent is not bonded to the surface of the tip and is mechanically entrained during the injection. In fact, the blooming agents used are not water soluble and they can be removed once the implant is injected only after a number of rinses.

The second drawback is linked to the migration kinetics of the blooming agent to the surface of the support. This phase can take several days, or even several weeks as a function of the utilization conditions (injection-moulding of the part), storage and post-treatment temperature, sterilization conditions etc. before a sufficient quantity of lubricant is located at the surface of the injection cartridge. The quality of the lubrication will therefore depend on the shelf life between the manufacture of the injector and the use thereof by the practitioner. If this period is too short, the lubrication is not carried out satisfactorily and if it is too long, the injected implant is covered with white patches (presence of blooming agent).

In order to remedy this drawback, the application WO 2005/018505 proposes thermally treating the parts in order to accelerate the blooming phenomenon and obtain a quasi-stable state (sufficient quantity of lubricant on the surface of the support) allowing reproducible injections.

Another route described by the U.S. Pat. No. 7,348,038 is a plasma treatment for ensuring a physical bond of the blooming agent to the cartridge.

The non-reproducibility of the lubrication and the presence of whitish patches on the implants after the injection represent the main defects of the use of these blooming agents.

A second approach ("coating" approach) allowing the sliding of the implants in the tips/cartridges of the injectors is the placing of a hydrophilic coating inside the tip. The principle of lubrication consists of causing the hydrophilic coating to swell by adding a viscous product (aqueous hyaluronate or hydroxypropyl-methylcellulose solution) and causing the implant to slide over a film of water formed at the interface.

The patents or patent applications JP56090838, JP3254752, U.S. Pat. No. 5,716,364, EP1949871, WO96/22062, WO2007/030009, WO2010/118080, U.S. Pat. No. 7,687,097, U.S. Pat. No. 7,348,038 and WO2010/059655 describe the possibility of producing a coating making it possible to reduce or eliminate the friction between the implant and the cartridge.

The hydrophilic coating is bonded to the surface of the tip/cartridge either by covalent chemical bonds or by physical bonds.

As regards the coatings bonded to the support by physical interactions, activation of the surface by a plasma or corona or other photochemical methods is systematically recommended as presented in the patents or patent applications JP56090838, JP3254752, EP1949871, U.S. Pat. No. 5,716,364, WO2010/059655, WO2010/118080 or U.S. Pat. No. 7,348,038. Once the surface is activated, the polymer in solution is deposited and the solvent is then evaporated off.

The hydrophilic polymers are, for example, chosen from polyacrylic acid, poly(methacrylic acid), polyvinyl acetate, polyacrylamide, polyvinylpyrrolidone, polyurethane and copolymers thereof, and sometimes a mixture of several of these polymers.

Coatings covalently bonded to the cartridge and the tip are moreover described in particular in the patents or patent applications EP 0 804 129, EP 0 952 796, U.S. Pat. No. 7,687,097 and WO96/22062. The approach recommended in particular in the documents U.S. Pat. No. 7,687,097 and WO96/22062 consists of immersing the cartridge, pretreated or not, through plasma in a precursor having reactive functions, for example acrylate groups, then subsequently radically (by thermal or UV irradiation) initiating the polymerization of the precursor, certain chains of which will react with the radicals formed at the surface of the cartridge.

As regards the "coating" approach, the slippery properties are constant over time and generally do not change as in the case of the blooming agents.

The major drawback of the methods which consist of coating the devices resides in the complex preparation of such coatings, in particular where the internal surface of the injectors is concerned. In fact this approach requires operating in several steps: i) activation of the surface, ii), deposition of the polymer film or polymerization/grafting then iii) evaporation of the solvent or unreacted compound and finally iv) checking the characteristics of the film (homogeneity/thickness), etc. These procedures significantly increase the production time and the cost of accessing devices possessing a slippery surface.

Other patents or patent applications such as EP 0 910 311, EP 1 198 207, U.S. Pat. No. 6,283,975, U.S. Pat. No. 6,398,788, U.S. Pat. No. 6,733,507, U.S. Pat. No. 6,679,891 and U.S. Pat. No. 6,083,230 also describe the possibility of using hydrophilic polymers as lubricating agents. Polyethylene glycol, polyvinylpyrrolidone, poly(N-vinyl lactame), polyacrylic acid, ethylene polyoxide, propylene polyoxide (mistakenly mentioned as a hydrophilic polymer), polyvinylpyridine (mistakenly mentioned as a hydrophilic polymer), polyvinyl alcohol, the polysaccharides, carboxymethyl cellulose, the hydroxyalkyl celluloses, poly (methacrylic) acid, polyacrylamide, polypeptides, sodium polystyrene sulphonate, polyhydroxyethyl methacrylate, heparin and mixtures thereof are mentioned in particular.

However, no clear indication is given concerning the utilization of these lubrication systems and their lubricity. Conversely, these applications mention, on the one hand, the presence of the lubricating polymer at the surface or close to the surface of the support and, on the other hand, physical interactions between the support and the lubricating polymer ("physically secured").

The major drawback of the use of the polymers mentioned in these patent applications is that the hydrophilic polymers used become detached from the support in many cases. They are thus entrained into the eye, the physical interactions with the support not being strong enough to prevent the solubilization of the hydrophilic polymer.

Another drawback of these methods is that they require subsequent treatment of the part of the device once prepared, in order to provide the sought lubrication (thermal post-treatment, plasma treatment, application of a coating), making preparation of the sliding device more expensive.

The Ozen et al, article, Polym. Bull., 2012, 68, 575-595 reports the study on compatibility and migration of an amphiphilic diblock copolymer poly(ethylene-ethylene oxide), having a molar mass of 2250 g/mole, containing 79 mass % ethylene oxide, in a polypropylene-co-ethylene copolymer (3.6 mass % ethylene). The objective is to increase the adhesion between polypropylene (PP) and polyimide (PA) layers in multilayer films, due to the migration of the amphiphilic copolymer at the interfaces. The migration, which was studied on model systems (films obtained by solvent evaporation, by extrusion or by blown film extrusion) is only observed when the PP surface is in contact with a glass plate, used as model for a PA layer.

The technical problem to be solved is therefore to provide a material comprising a mixture of polymers making it possible to confer both the desired mechanical properties and lubrication properties, for the preparation of ophthalmic injectors and more particularly that of the tip/cartridge, in order that the latter have sliding and stability qualities capable of conferring comparable properties on the coated cartridges/tips while reducing the number of steps, and therefore the costs, of manufacture. The solution must also take into account the creation of strong interactions between the constituent material and the polymer allowing the lubrication, in order to prevent or at least limit any solubilization and/or entrainment of the lubricating polymer into the patient's eye.

In the remainder of the description, the terms "ophthalmic injector" or "ophthalmic implant injection device" will be used interchangeably.

The terms <<slipping>> or <<slipperiness>> will also be used interchangeably.

A subject of the present invention is, in particular, the direct provision of the required properties of slipperiness to devices for the injection of ophthalmic implants (or intraocular lenses) through a micro-incision during the processing phase (preparation by injection/moulding). The invention also makes it possible to remedy the drawbacks and defects caused by the different post-treatment methods described previously. These objectives are achieved by the use of novel polymer compositions constituted by mixtures of polymers and copolymers having particular characteristics and possessing a metastable morphology capable of leading directly, during the utilization of the devices, to properties of slipperiness allowing the injection of intraocular lenses through a micro-incision.

A subject of the invention is therefore these particular metastable polymer compositions, the method of preparation of the devices or device components with a slippery surface, the devices with a slippery surface resulting from these metastable compositions and their uses as injection systems for intraocular lenses through a micro-incision of 3 mm or less.

By "metastable polymer compositions" is meant mixtures of two or more partially miscible or compatible polymers or copolymers (as defined by the IUPAC in the journal Pure Appl. Chem., Vol 76, No. 11, pp 1985-2007, 2004) capable of leading to more stable polymer materials with multiphase morphology and which are set in a metastable morphological structure.

By "metastable morphology" is meant a system outside its morphological equilibrium state, the evolution kinetics of which towards its thermodynamically stable form is extremely slow under given conditions and can be ignored within a specific time scale.

This evolution in morphological organization can however be brought about by supplying energy to the system, such as for example by a sufficient rise of its temperature for a limited time. In the particular case of a mixture of partially miscible or compatible polymers the morphology is referred to as "metastable" when the processes of segregation of the phases by migration of the polymer or copolymer chains are not completed and will not change, or only negligibly, under given temperature conditions and within a specific time scale.

This definition includes mixtures having apparently single-phase morphologies, corresponding to a macroscopically uniform distribution of the different polymer components as well as of the transitory bi- or multiphase morphologies, which will change when the temperature of said mixtures is raised sufficiently.

It is well known, moreover, that if the mobility of the polymer chains depends on the temperature, it also depends on the physical state in which said polymers are found.

For an amorphous polymer the mobility of the chains will in particular depend on its glass transition temperature (Tg), corresponding to the transition from the glassy state to the visco-elastic state.

For a crystalline or semi-crystalline polymer, mobility is determined by the melting temperature (Tm).

In the case of a mixture of partially miscible or compatible polymers, below the Tg/Tm of each of the constituents the mobility of the chains is greatly reduced, preventing any morphological rearrangement such as phase separation over a very large time scale. The further the temperature below the Tg(s)/Tm(s), the more immobile and set the system. Conversely, above the Tg(s)/Tm(s), the chains acquire a mobility allowing their migration within the material, causing its morphology to change towards a thermodynamically more stable multiphase organization.

If the case of certain polymers which become miscible at high temperature (systems having a higher critical solubility temperature), the higher the temperature above the Tg(s)/Tm(s), the greater the mobility of the chains and the more rapid the morphological reorganization kinetics of the mixture.

For a given polymer in a mixture of partially miscible or compatible polymers, the diffusion/migration of the chains is also dependent on its molar mass; the lower the molar masses of the chains, the more rapid the migration kinetics.

Finally, the migration of the polymer chains in a mixture depends on the nature of the compatibility/miscibility between said chains, it slows down when the compatibility between polymers increases. Partial miscibility, as described in the application WO2009/156628, leads, in addition to phase separation, to the creation of microdomains which are characterized by specific transition temperatures where the different chains are in close molecular interaction. These microdomains make it possible to establish links between the phases by chain entanglements. These links slow down the diffusion/migration of the chains around the Tg(s)/Tm(s) and, at these temperatures, reinforce the set nature of the metastable compositions. However, they have negligible effects on the diffusion at temperatures much higher than the Tg(s)/Tm(s) of the different phases and microdomains.

The metastable compositions according to the invention are obtained from mixtures of partially miscible or compatible polymers and copolymers. These mixtures are characterized by a bi- or multiphase morphology, and by the presence of interphases constituted by chains of the constituent polymer and hydrophobic sequences or blocks of the functional copolymer. The polymers and copolymers moreover have certain specific characteristics which are indicated below. The corresponding mixtures, obtained by compounding, are characterized by a metastable morphological state. They are composed in particular:

1) of at least one thermoplastic polymer forming the structure and conferring the mechanical properties, the so-called "constituent polymer".

It has a high molar mass, in particular greater than 40000 g/mole, preferably greater than 100000 g/mole, and a high Tg or Tm, in particular above or equal to 80° C., and preferably above or equal to 100° C.

This first polymer, which serves to give the material and the parts or devices prepared from said mixture their mechanical characteristics, is in the majority proportion by mass and, preferably, in a proportion by mass comprised between 85% and 99.9% and more particularly between 90% and 99.5% by mass.

This constituent polymer is preferably chosen from the polyolefins, and more particularly polypropylene, the polyamides, polyurethanes and polyesters.

These constituent polymers are utilized by injection/moulding at temperatures comprised between 160° C. and 300° C.

2) at least one so-called "functional" copolymer, partially miscible or compatible with the abovementioned constituent polymer; the partially miscible or compatible nature being ensured by sequences or blocks of chosen co-monomers with a hydrophobic character.

Advantageously, said constituent polymer provides the mechanical properties and said functional copolymer makes the material prepared from said mixture slippery, in particular when it is put in the presence of an aqueous solution or suspension.

The functional polymers serve to provide the material and the parts or devices prepared from said mixture with specific properties, in particular surface properties. Thus the slippery properties sought for the injection devices of intraocular lenses are preferably obtained with copolymers possessing mainly blocks or sequences with a hydrophilic character and a minority proportion of the hydrophobic sequences or blocks providing partial compatibility with the first polymer; the hydrophilic blocks representing more than 60% of the copolymer.

The slippery properties will show by adding an aqueous solution or suspension in which the intraocular lens is immersed into the injection device, and which forms a superficial water layer stabilized by hydration of the hydrophilic blocks of the functional copolymer which are located at the surface of the material formed from the composition of the invention. This liquid interface between said material and the intraocular lens will considerably reduce the friction phenomenons and provide the slippery character which allows the injection of the lens through the small diameter-tip of the injection device under low stress.

In particular, the intraocular lens can be introduced in the presence of an aqueous solution of hyaluronic acid, hyaluronate, hydroxypropylmethyl cellulose or any other hydrophilic viscous agent.

This solution is added between about 30 s and 5 min before injecting the implant through the micro-incision, as indicated earlier.

The "slippery character" of the material prepared from the metastable composition described above can be measured, for example, using a single-part ophthalmic injector manufactured entirely by injection/moulding from said composition or an injector made up of two parts in which only the loading cartridge and the tip are manufactured from said composition. The thrust force on the plunger of the injector necessary to eject the implant loaded in the cartridge of the injector through a tip with an outlet diameter of less than 3 mm, for example 2 mm, is measured. This measurement can be carried out by compression by means of an Instron 3367-type dynamometer equipped with a force sensor having a sensitivity of 0.5 kN at a speed of 8.5 mm/s. It is considered that the slipping property is high and non-traumatic in the case of force values comprised between 1 and 5 N. It is moderate in the case of force values higher than 5 N and lower than 10 N, and low for force values higher than 10 N.

Thus, it is considered that a material prepared from the metastable composition of the invention provides the ophthalmic injector with a "slippery character" when a practitioner injects without damage an implant having a diopter lower or equal to 30 D in the patient's eye, while applying a force which is lower than or equal to 5 N.

The molar mass and the relative sizes of the sequences or blocks which contribute to the hydrophilic/hydrophobic balance of the copolymers are, preferably, selected in order, on the one hand, to optimize their partial compatibility with the material based on the constituent polymer (for example, PP or PA), and, on the other hand, to allow their migration and their interaction with the external aqueous medium, thereby providing a hydrophilic character to the surface of the material, which promotes the creation of a superficial water layer, while the interactions of the hydrophobic sequences or blocks of the functional copolymer with the material based on the constituent polymer prevents the possible solubilization of the polymer in the aqueous solution.

An estimation of the hydrophilic/hydrophobic balance can be made by studying the copolymers' micellization, where those forming stable micelles possess an appropriate structure which fulfills the desired surface and slippery characteristics.

The functional copolymers according to the invention possess molar masses greater than 5000 g/mol, preferably comprised between 10000 and 100000 g/mol, and in particular preferably between 10000 and 40000 g/mol. Selecting copolymers possessing a molar mass greater than 5000 g/mol makes it possible to limit their solubilization in the aqueous phase.

These copolymers must moreover possess Tg(s) or Tm(s) comprised within a range of temperatures above or equal to 40° C., and below the Tg or Tm values of the constituent polymers. They must also possess a thermal stability, at the processing temperature of the constituent polymer, generally comprised between 160° C. and 300° C., making it possible for them to withstand the conditions of processing by injection-moulding without chemical or structural degradation.

The functional copolymers which provide slippery properties can be chosen from random copolymers, block copolymers, comb copolymers and star copolymers. They can preferably be chosen from the polyethers, polyesters and polyurethanes having both hydrophilic and hydrophobic sequences or blocks and from copolymers based on (meth) acrylic acid, (meth)acrylate, ethylene oxide, acrylamide, vinyl alcohol, vinyl pyrrolidone or hydroxyethyl(meth)acrylate combined with hydrophobic units partially miscible or compatible with the constituent polymer.

Moreover, these functional copolymers preferably have a majority hydrophilic proportion, preferably at least 60% by mass of hydrophilic monomer units, in particular between 60 and 99% by mass of hydrophilic monomer units and in particular between 70 and 97% by mass of hydrophilic monomer units.

The role of the minority hydrophobic sequences or blocks is, on the one hand, to limit the risks of solubilization of the copolymer in aqueous medium and, on the other hand, to provide partial miscibility or compatibility with the constituent polymer.

There may be mentioned, by way of example, the existence of partial compatibility between the propylene polyoxide and polypropylene blocks, or between the polycaprolactone and polypropylene sequences, or finally between polyester and polyamide sequences.

It is also possible to use a functional copolymer which possess, in addition to the above-mentioned characteristics, reactive groups which are able to react with the thermoplastic polymer during the processing step by injection/moulding.

In such case, the functional copolymers possess reactive groups which, for example, will react by radical route (thermic, or else photochemical) with radicals which are created on the chains of the constituent polymer.

The metastable polymer compositions according to the invention are prepared by compounding and extrusion in order to obtain these compositions in various forms: beads, granules, which can be directly utilized for injection/moulding, in order to produce devices possessing the sought slippery properties in a single step.

These metastable compositions have the advantage and the feature of being, depending on the temperature conditions:

either in a set metastable state in which they can be stored without any evolution in their morphology over a duration of several months or even several years. This state corresponds to the range of temperatures below the Tg/Tm of the different polymer components of the mixture, or in an "activated" state, i.e. subjected to conditions of rapid evolution, towards a multiphase, thermodynamically more stable morphology. This activated state corresponds to high temperatures, above the Tg/Tm of the polymer constituents, temperatures at which the mobility of the chains is optimum.

In the invention, this activation/evolution is carried out during the time of processing of the devices at high temperature, typically a few seconds to a few minutes at injection-moulding temperatures comprised between 160° C. and 300° C. This operation results directly in a device produced from a multiphase material characterized in that the matrix comprises or is constituted by the first polymer, the so-called constituent polymer, whereas the second so-called functional polymers form domains distributed non-homogeneously between the core and the surface of the material, in particular giving the device surface properties such as slipperiness.

The invention also relates to the materials, parts or devices obtained from the metastable polymer compositions described above which, advantageously, possess, in the presence of water, the required surface property, in particular the slippery character. Advantageously, said materials, parts or devices can be produced in one step by injection/moulding from metastable polymer compositions described above.

Another advantage of the invention is that a surface property is obtained, which makes it possible to obtain slipperiness characteristics which remain stable and constant over a long time scale, from the preparation of the parts or devices by injection/moulding to the use of the device by the practitioner. The slippery character is obtained at any time by only adding a viscous agent solution. This surface property is maintained by the simple condition of keeping the part or device at temperatures below the glass transition or melting temperatures of the different polymer components, which is easily achieved when the polymers and copolymers used have a Tg or Tri above the usual storage temperatures of the devices, temperatures which are very generally below 50° C., preferably below 40° C.

Another advantage of the invention results from the use of functional copolymers possessing both hydrophilic units and hydrophobic units. The optimization of the hydrophilic/hydrophobic balance of the copolymer makes it possible to prevent its solubilization in aqueous medium. This character is reinforced by the miscibility of the hydrophobic sequences with the constituent polymer, which limits diffusion/migration at the storage and use temperatures of the parts or devices, without however affecting the phase separation which takes place during the processing by injection-moulding of the part of the device. These characteristics ensure great stability over time for the system and limit any entrainment of the functional copolymer during the injection of the implant by the practitioner.

According to a particular aspect of the invention, a covalent bond between the thermoplastic constituent polymer and the hydrophilic copolymer function can be produced during the injection/moulding process using reactive groups fixed to the functional copolymer. This has the particular advantage of obtaining a device having a slippery surface which is even more stable in aqueous medium. The benefit of this approach relates in particular to injection systems containing implants pre-loaded into a cartridge containing a physiological liquid.

In order to achieve permanent grafting, it is possible to use a functional copolymer having, in addition to the above-mentioned characteristics, reactive groups capable of reacting with the thermoplastic polymer during the operation of processing by injection/moulding.

For this particular method, the functional copolymers are provided with reactive groups which, for example, will react radically (thermally or photochemically) with the radicals created on the chains of the constituent polymer. These reactive groups can, for example, be meth(acrylate) functions capable of reacting in the presence of a radical initiator during utilization at above 160° C., a process which is similar to reactive injection/moulding. The initiator which will make it possible to initiate the radical polymerization can be introduced into the extruder with the metastable composition.

In certain cases, it may be preferable to carry out these covalent coupling reactions between the functional copolymer and the constituent polymer, after the phase segregation within the mixture is carried out. In this case it is possible to use a two-input extruder, which makes it possible to introduce firstly the metastable composition, then subsequently the radical-generating derivative.

Another approach for this particular aspect of the invention, consists of using a photoinitiator. The latter can be introduced at the same time as the metastable composition constituted by the constituent polymer (for example, polypropylene) and the functional copolymer having meth(acrylic) groups. The processing operation is then accompanied, during removal from the mould, by irradiation (UV, gamma) of the device causing the photochemical bonding of the slippery polymer.

The invention also relates to the materials, parts or devices prepared from the metastable polymer compositions described earlier, in particular prepared by injection/moulding, such as, in particular, a medical device part or a medical device. In particular, said part is all or part of an ophthalmic implant injection device (ophthalmic injector), for example a tip or a cartridge, or a tip/cartridge part of an ophthalmic injector.

The invention also relates to the ophthalmic implant injection devices comprising at least one part prepared from a metastable composition described above.

The invention also relates to a method for manufacturing a material, a medical device part or a medical device, which comprises a step of injection/moulding of a metastable composition as described above.

The present invention differs significantly from the prior art describing the use of blooming agents, in the following ways:

The blooming agents are organic molecules of low molar masses of lipophilic and/or surfactant nature, whereas, according to the invention copolymers of high molar masses are used, preferably greater than 5000 g/mol, capable of forming a material with multiphase morphology.

The blooming agents migrate to the surface of the constituent material over time, which means that the properties of slipperiness change as a function of the duration of storage and use of the device by the practitioner. They also depend on optional thermal post-treatments, the method of sterilization, etc. Conversely, according to the invention, the multiphase morphology is obtained during the manufacture of the single-part injector or the tip/cartridge of the injectors made up of two parts. The properties of slipperiness can therefore be generated by the simple addition of an aqueous solution as from the processing step while, for the reasons mentioned previously, they do not change over time.

The surface blooming agents, which are not bonded to the constituent thermoplastic polymer, are entrained into the eye during the injection of the implant. Their lipophilic and/or surfactant character makes them insoluble in water and leads to their being deposited on the surface of the implant in the form of white traces. These deposits must be completely removed at the risk of impairing the optical quality of the implant put into place, which is not a problem in the case of the present invention.

The present invention also differs completely from the "coating" approach. The latter, which consists of depositing a polymer film on the surface of the device or certain of its components, requires several operations to be carried out, including the activation of the surface, putting the hydrophilic polymer in solution and evaporation of the solvent. The approach proposed in the present invention makes it possible to avoid all these steps in the manufacturing process and leads to simplification of the method to the single step of processing by injection.

Finally, the present invention differs from the prior art which consists of combining, by simple physical interactions, the constituent polymer with hydrophilic or even water-soluble homopolymers, as a lubricating agent. The invention firstly differs in the nature of the copolymers used which possess both sequences with a hydrophilic character and hydrophobic sequences and the hydrophilic/hydrophobic balance of which makes it possible to limit solubilization during the injection. Secondly, the invention differs in that the hydrophobic sequences or blocks of functional copolymers are partially miscible or compatible with the constituent polymer which leads to the formation of common microdomains ensuring a bond between the phases under conditions of storage and use. These characteristics of the copolymers of the invention provide a stability of the properties of slipperiness and prevent any entrainment into the eye of the patient.

The following examples illustrate the invention non-limitatively.

Examples 1 to 5 relate to the preparation of functional copolymers making it possible to obtain, in a mixture with a constituent polymer, a metastable composition according to the invention.

Examples 6 and 7 relate to the preparation of functional copolymers possessing reactive groups making it possible to obtain, in a mixture with a constituent polymer, a metastable composition according to the invention and moreover having the feature of being able to be chemically grafted onto the constituent polymer.

Examples 8 to 13 relate to the preparation of the metastable compositions according to the invention, use thereof for manufacturing ophthalmic injector cartridges and the characterization of the properties of slipperiness of these injectors for the injection of ophthalmic implants.

EXAMPLE 1

Preparation of a Polyurethane Urea Based on Poly(Ethylene Oxide-b-Propylene Oxide-b-Ethylene Oxide) (PEO-PPO-PEO) Tribiock Copolymers Terminated by Acid Units The synthesis is carried out in two steps. In a first step, $3.8 \cdot 10^{-3}$ mole of F127 Pluronic® polymer, not dried, containing 0.3% by mass of water is dissolved in 150 ml of 2-butanone. Then $1.5 \cdot 10^{-2}$ mole of 4,4'-methylene biscyclohexyl di-isocyanate is added dropwise over 10 minutes under a continuous flow of nitrogen. When approximately 81% of the isocyanate functions have been consumed (monitored by Fourier transform infrared spectroscopy), $2.9 \cdot 10^{-3}$ mole of 2,2-bis(hydroxymethyl) butyric acid is added. Polycondensation continues for 2 hours at 70° C. until the isocyanate functions have completely disappeared. The copolymer is collected by precipitation from diethyl ether and dried under vacuum at ambient temperature.

The copolymer has a melting temperature of 52° C. Analysis by steric exclusion chromatography (SEC) indicates the presence of chains of copolymers with molar masses greater than 10,000 g/mol (polystyrene calibration).

EXAMPLE 2

Preparation of a Polyurethane Urea Based on Copolymer PEO-PPO-PEO Terminated at its Ends by PEO Chains $7.69 \cdot 10^{-3}$ mole of Pluronic F127 is dried under vacuum at 80° C. over 2 hours then solubilized in 300 ml of 2-butanone containing 0.2 g of water. $15.84 \cdot 10^{-3}$ mole of 4,4' methylene biscyclohexyl di-isocyanate is then added dropwise over 10 minutes under a continuous flow of nitrogen. 500 ppm of a tin-based catalyst are introduced after 30 minutes following the addition of isocyanate. $13.98 \cdot 10^{-3}$ mole of a monohydroxylated poly(ethylene oxide) with a molar mass equal to 600 g/mol is introduced when 58% of the isocyanate functions have disappeared (monitored by Fourier transform infrared spectroscopy). The reaction is continued until the isocyanate functions have completely disappeared and can take up to 12 hours. The copolymer is then precipitated from a non-solvent (petroleum ether) then dried under vacuum at 40° C.

The copolymer has a melting temperature of 52° C. SEC analysis (polystyrene calibration) indicates the presence of chains of copolymers with molar masses greater than 10,000 g/mol.

EXAMPLE 3

Preparation of a Copolyurethane Based on Poly(Ethylene Oxide) and Poly(ε-Caprolactone)

400 g of a dihydroxytelechelic PEO with a molar mass of 6000 g/mol ($6.67 \cdot 10^{-2}$ mole) and 100 g of a dihydroxytelechelic poly(ε-caprolactone) (PCL) ($8 \cdot 10^{-2}$ mole) with a molar mass of 1,250 g/mol, are dried under vacuum for 2 hours at 100° C. then solubilized in 1.45 liters of 2-butanone previously dried over $CaCl_2$. The solution is cooled down to 85° C. during the introduction of 38.43 g ($14.67 \cdot 10^{-2}$ mole) of Desmodur W di-isocyanate marketed by Bayer. 0.5 g of a bismuth-based catalyst is added 5 minutes after completion of the introduction of the isocyanate.

The reaction is terminated after 19 hours by the addition of 1 ml of ethanol. The solution is then cooled down to ambient temperature then diluted in 1.5 liters of acetone then precipitated from 8 liters of heptane.

The molar mass by number of the polymer obtained (PS equivalent) 25000 g/mol. The multiblock-type copolymer has a block melting temperature ranging from 40 to 53° C.

EXAMPLE 4

Preparation of a Poly(Methylmethacrylate-Co-Polyethyleneoxide Methacrylate) Random Copolymer 200 g of polyethylene glycol methacrylate (MAPEG with a molar mass of 1100 g/mol) are solubilized in 800 ml of 2-butanone at ambient temperature over 1 hour 30 minutes. 1.6 g of 2,2'-azobis 2-methylbutane nitrile (radical initiator) is added to the medium which is then heated to 100° C. just before the addition of 20 g of methyl methacrylate (MMA). The reaction medium is left at 100° C. for 4 hours, then precipitated from heptane and dried under vacuum at 40° C. The molar mass by number (PS equivalent) of the polymer obtained is 31000 g/mol. It exhibits in particular a Tm of approximately 50° C. of the ethylene polyoxide blocks.

EXAMPLE 5

Preparation of a Poly(Vinylpyrrolidone-Co-2-Hydroxyethylmethacrylate-Co-Polyester Methacrylate) Random Copolymer a) Synthesis of Polyester Methacrylate (FTL11228)

200 g of ε-caprolactone, 67.66 g of 2-hydroxyethyl methacrylate and 0.759 g of a tin-based catalyst are solubilized in 216 ml of distilled anhydrous toluene. The system is heated at 90° C. for 18 hours. The recovered macromonomer, characterized by proton NMR, has a molar mass of 562 g/mol.

b) Synthesis of the Poly(Vinylpyrrolidone-Co-2-Hydroxyethylmethacrylate-Co-Polyester Methacrylate) Random Copolymer 1—66.53 g of 2-hydroxyethyl methacrylate, 7.24 g of FTL 11228 polyester methacrylate and 1.18 liters of technical-grade ethanol are introduced into a reactor equipped with a condenser with a bubbler under a light flow of nitrogen. This first mixture is called a "starter".

2—A second mixture is prepared alongside, constituted by 59.69 g of 1-vinyl 2-pyrrolidone, 28.96 g of FTL 11228 polyester methacrylate, 216 g of 2-hydroxyethyl methacrylate, 19.29 g of dodecanethiol, 5.79 g of AIBN and 415 ml of technical grade ethanol. This mixture No. 2 is left under stirring until solubilized.

3—Mixture No, 2 is poured dropwise over 60 minutes onto the starter taken to reflux.

4—The mixture is left under reflux under a light flow of nitrogen for 3 hours 30 minutes as from the end of pouring.

5—The final medium is left to cool down, reconcentrated, precipitated from water and lyophilized.

The copolymer obtained has a Tg of 63° C.
The molar masses determined by Size Exclusion Chromatography (solvent DMF/LiBr-Column DMFext-PS calibration) of the copolymer are Mw=22,000 g/mol; Mp=21,420 g/mol; Mn=13,900 g/mol; and the polydispersity index is 1.6.

EXAMPLE 6

Preparation of a Polyurethane Copolymer Based on PEO and PCL Terminated by Acrylate Units at Both its' Ends 400 g of a dihydrotelechelic PEO with a molar mass=6000 g/mol ($6.67 \cdot 10^{-2}$ mole) and 100 g of a dihydroxytelechelic poly($\epsilon$-caprolactone) (PCL) ($8 \cdot 10^{-2}$ mole) with a molar mass of 1250 g/mol are dried under vacuum for 2 hours at 100° C. then solubilized in 1.45 l of dried 2-butanone. 34 g of Desmodur W (di-isocyanate) and 0.5 g of a bismuth-based catalyst are added to the reaction medium which is heated to 85° C.

After complete consumption of the isocyanates, the reaction medium is cooled down and 2 g of acryloyl chloride is added to the reaction medium. The reaction is stopped 2 hours after the addition of the acryloyl chloride. The polymer is then precipitated from ether. Analysis by Fourier transform infrared spectroscopy (FTIR) shows the presence of unsaturations on the polymer chains. The multiblock-type copolymer has a block melting temperature ranging from 40 to 53° C.

EXAMPLE 7

Preparation of a Polyvinylpyrrolidone-Co-2-Hydroxyethylmethacrylate-Co-Polyester Methacrylate) Random Copolymer Bearing Pendant Acrylate Groups 100 g of copolymer of Example 6 is solubilized in 500 ml of dry THF, 2 g of acryloyl chloride is added to the solution at ambient temperature. After 4 hours, the reaction is stopped and the copolymer precipitated from heptane. FTIR analysis shows the presence of acrylic-type unsaturations on the copolymer chains.

EXAMPLE 8

A reference polypropylene PPR 10222 marketed by TOTAL is mixed (or "compounded") with the copolymer described in Example 2 under the following conditions:
  Twin-screw extruder Ø 26 mm L=50 D
  Flow rate: 10 kg/h
  Screw speed: 300 rpm
  Temperature profile: (base) 210-210-200-190-180-170-170-160-160-160 (die): programmed in this way because of the very great fluidity of the compound obtained. The temperature is lowered in the die to approximately the melting temperature of the PP. Each temperature block is 5 D in length.

The 2 polymer components are mixed and introduced via a gravimetric doser into the base of the extruder. The copolymer of Example 2 is mixed with the polypropylene PPR 10222 in percentages of 1, 2, 5 and 10%. The different metastable compositions obtained ("compounds") are recovered at the extruder exit in the form of granules and stored at ambient temperature.

The different metastable compositions obtained are then processed by injection/moulding in order to manufacture cartridges/tips of ophthalmic implant injectors with an outlet diameter of 2 mm.

The slipperiness properties were evaluated on the injectors corresponding to regular intervals over 2 months after their date of manufacture. The tests were carried out with 27 D diopter hydrophilic implants made from hydroxyethylmethacrylate (HEMA) (water content 28%) after the addition of an aqueous solution of hyaluronate (0.1 to 0.2 ml, HA at 2.1%). Comparative tests were carried out under the same conditions on cartridges/tips made of polypropylene (PPR10222) compounded with glycerol monostearate (GMS).

The slippery character was determined from the compression force needed for injecting the implant through the 2 mm exit diameter. These measurements were carried out with an Intron 3367-type dynamometer equipped with a 0.5 kN sensor, at a compression speed of 8.5 mm/s. The results are classified as a function of force in three categories: low, moderate, high. The results are shown in Table 1 below.

TABLE 1

| No. | Nature of the cartridge/tip | Test carried out 1 day after the processing step* | Test carried out 7 days after the processing step* | Test carried out 15 days after the processing step* | Test carried out 1 month after the processing step* | Test carried out 2 months after the processing step* |
|---|---|---|---|---|---|---|
| 1.1 | PP + GMS | Low slipperiness | Moderate slipperiness | High slipperiness. Presence of white traces. | High slipperiness. Presence of white traces. | High slipperiness. A lot of white traces. |
| 1.2 | PP + 1% of the copolymer of Example 2 | Moderate slipperiness | Moderate slipperiness | Moderate slipperiness | Moderate slipperiness | Moderate slipperiness |
| 1.3 | PP + 2% of the copolymer of Example 2 | High slipperiness | High slipperiness | High slipperiness | High slipperiness | High slipperiness |

TABLE 1-continued

| No. | Nature of the cartridge/tip | Test carried out 1 day after the processing step* | Test carried out 7 days after the processing step* | Test carried out 15 days after the processing step* | Test carried out 1 month after the processing step* | Test carried out 2 months after the processing step* |
|---|---|---|---|---|---|---|
| 1.4 | PP + 5% of the copolymer of Example 2 | High slipperiness | High slipperiness | High slipperiness | High slipperiness | High slipperiness |
| 1.5 | PP + 10% of the copolymer of Example 2 | High slipperiness | High slipperiness | High slipperiness | High slipperiness | High slipperiness |

*Each test is carried out 3 times in order to validate the result obtained
Low slipperiness: possibly leading to significant degradation of the implants (Applied force > 10N)
Moderate slipperiness: requiring a high force for the injection with the risk of alteration of the implants (5N < Applied force < 10N)
High slipperiness: allowing easy injection without risk of alteration of the implants (1N < Applied force < 5N)

The results show that the tips manufactured from the metastable composition (polypropylene (PP)+copolymer of Example 2) exhibit properties of slipperiness which are constant over time, which is not the case with the tips containing GMS. This slipperiness is high for metastable compositions containing more than 1% of the copolymer of Example 2. The Ups containing 5 and 10% functional copolymer are more opaque than their homologues containing 1 and 2% of the copolymer of Example 2.

For all the cartridges/tips prepared from metastable compositions (PP+polymer of Example 2), no traces are observed on the implant after injection.

EXAMPLE 9

The same cartridges/tips are used for injection tests with a 25 D diopter flexible hydrophobic implant.
The results are shown in Table 2 below.

TABLE 2

| No. | Nature of the cartridge/tip | Test carried out 1 day after the processing step * | Test carried out 7 days after the processing step * | Test carried out 15 days after the processing step * | Test carried out 1 month after the processing step * | Test carried out 2 months after the processing step * |
|---|---|---|---|---|---|---|
| 2.1 | PP + GMS | Low slipperiness | Low to moderate slipperiness | Moderate to high slipperiness Presence of traces | High slipperiness Presence of traces | High slipperiness A lot of traces |
| 2.2 | PP + 1% of the copolymer of Example 2 | High slipperiness | High slipperiness | High slipperiness | High slipperiness | High slipperiness |
| 2.3 | PP + 2% of the copolymer of Example 2 | High slipperiness | High slipperiness | High slipperiness | High slipperiness | High slipperiness |
| 2.4 | PP + 5% of the copolymer of Example 2 | High slipperiness | High slipperiness | High slipperiness | High slipperiness | High slipperiness |
| 2.5 | PP + 10% of the copolymer of Example 2 | High slipperiness | High slipperiness | High slipperiness | High slipperiness | High slipperiness |

* Each test is carried out 3 times in order to validate the result obtained.
Low slipperiness: possibly leading to significant degradation of the implants (Applied force > 10N)
Moderate slipperiness: requiring a high force for the injection with the risk of alteration of the implants (5N < Applied force < 10N)
High slipperiness: allowing easy injection without risk of alteration of the implants (1N < Applied force < 5N)

The results show that the tips/cartridges prepared in the presence of the copolymer of Example 2 exhibit the same properties of slipperiness with the hydrophilic implants as with the hydrophobic implants.

EXAMPLE 10

A commercial reference polypropylene, PPR 10222, from Total is mixed ("compounded") with the copolymer of Example 3 introduced in percentages of 1, 2 and 5% under the following conditions:

Twin-screw extruder 026 mm L=50 D
Flow rate: 10 kg/h
Screw speed: 300 rpm
Temperature profile: (base) 210-210-200-190-180-170-170-160-160-160 (die): programmed in this way because of the very great fluidity of the compound obtained. The temperature is reduced in the die to approximately the melting temperature of the PP. Each temperature block is 5 D in length.

The 2 polymer components are mixed and introduced via a gravimetric dower into the base of the extruder. The different metastable compositions obtained ("compounds") are recovered at the extruder exit in the form of granules and stored at ambient temperature.

The different metastable compositions obtained are then processed by injection moulding in order to manufacture cartridges/tips of ophthalmic implant injectors with an outlet diameter of 2 mm. No problem with removal from the mould is noted during the processing step.

The slipperiness measurements were evaluated on the injectors at regular intervals over 2 months after their date of manufacture. All the injection tests were carried out with 28 D diopter HEMA hydrophilic implants (28% water content) after the addition of a viscous agent, hyaluronic acid. Two reference cartridges/tips made from PP were used as a comparison. The first contains 025% GMS, the second, following plasma treatment, is coated with a hydrophilic polymer.

The results are shown in Table 3 below. The cartridges/tips manufactured in one step from metastable compositions of PP+copolymer of Example 3 exhibit properties of slipperiness comparable to those of the cartridges/tips treated with plasma then coated with a hydrophilic polymer of Example 8 using a mould temperature of 4550° C. The prepared tips also have an outlet diameter of 2 mm.

As regards the properties of slipperiness, the implant injection tests were carried out with 27 D diopter hydro-

TABLE 3

| No. | Nature of the cartridge/tips | Test carried out 1 day after the processing step * | Test carried out 7 days after the processing step * | Test carried out 15 days after the processing step * | Test carried out 1 month after the processing step * | Test carried out 2 months after the processing step * |
|---|---|---|---|---|---|---|
| 3.1 | PP + GMS | Low slipperiness | Low to moderate slipperiness | Moderate to high slipperiness | High slipperiness Presence of traces | High slipperiness A lot of traces |
| 3.2 | PP + hydrophilic coating | High slipperiness | High slipperiness | High slipperiness | High slipperiness | High slipperiness |
| 3.3 | PP + 1% of the copolymer of Example 3 | High slipperiness | High slipperiness | High slipperiness | High slipperiness | High slipperiness |
| 3.4 | PP + 2% of the copolymer of Example 3 | High slipperiness | High slipperiness | High slipperiness | High slipperiness | High slipperiness |
| 3.5 | PP + 5% of the copolymer of Example 3 | High slipperiness | High slipperiness | High slipperiness | High slipperiness | High slipperiness |

* Each test is carried out 3 times in order to validate the result obtained.
Low slipperiness: possibly leading to significant degradation of the implants (Applied force > 10N)
Moderate slipperiness: requiring a high force for the injection with the risk of alteration of the implants (5N < Applied force < 10N)
High slipperiness: allowing easy injection without risk of alteration of the implants (1N < Applied force < 5N)

As regards the tips/cartridges prepared from the metastable compositions of PP+copolymer of Example 3, lubrication comparable to the coating route as well as the absence of any traces on the injected implants can be noted. The main advantage of this approach compared with the "coating" route is the great simplicity of making use of it.

EXAMPLE 11

A PEBAX 7033-type polyimide from Arkema is mixed ("compounded") with the copolymer of Example 3.

The preparation of the metastable compositions is carried out according to the protocol of Example 8 using an injection temperature of 260° C.

Similarly, the cartridges/tips produced from these metastable compositions are prepared according to the protocol philic implants made from HEMA (28% water content) after the addition of a viscous agent, hyaluronic acid.

Two reference cartridges/tips, the first manufactured from the same PEBAX loaded with 0.25% by mass of GMS, the second constituted by a PEBAX cartridge/tip coated with a hydrophilic polymer were used in order to allow comparison with the existing systems.

The results are shown in Table 4 below.

TABLE 4

| No. | Nature of the cartridge/tip | Test carried out 1 day after the processing step * | Test carried out 7 days after the processing step * | Test carried out 15 days after the processing step * | Test carried out 1 month after the processing step * | Test carried out 2 months after the processing step * |
|---|---|---|---|---|---|---|
| 4.1 | PA** + GMS | Low slipperiness | Low slipperiness | Moderate slipperiness | High slipperiness Presence of traces | High slipperiness Presence of traces |
| 4.2 | PA + hydrophilic coating | High slipperiness | High slipperiness | High slipperiness | High slipperiness | High slipperiness |
| 4.3 | PA + 1% copolymer of Example 3 | High slipperiness | High slipperiness | High slipperiness | High slipperiness | High slipperiness |
| 4.4 | PA + 2% copolymer of Example 3 | High slipperiness | High slipperiness | High slipperiness | High slipperiness | High slipperiness |
| 4.5 | PA + 5% copolymer of Example 3 | High slipperiness | High slipperiness | High slipperiness | High slipperiness | High slipperiness |

* Each test is carried out 3 times in order to validate the result obtained,
**PA = polyamide
Low slipperiness: possibly leading to significant degradation of the implants (Applied force > 10N)
Moderate slipperiness: requiring a high force for the injection with the risk of alteration of the implants (5N < Applied force < 10N)
High slipperiness: allowing easy injection without risk of alteration of the implants (1N < Applied force < 5N)

The results show that the injected implants using cartridges/tips manufactured from the metastable composition PP+copolymer of Example 3 slip perfectly and can easily be introduced through a 2 mm incision. The slipperiness which characterizes these cartridges/tips is in every way comparable to, or even better than that of the cartridges/tips coated with a hydrophilic polymer.

EXAMPLE 12

The cartridges/tips described in Example 11 served to inject 26 D diopter hydrophobic flexible implants; the protocol used is similar to that described for the hydrophilic implants.

Implant injection tests are then carried out at regular intervals, namely after one day, 7 days, 15 days, 30 days and 60 days of immersion. The results are summarized in Table 5 where they can be compared to those obtained with a commercially available cartridge/tip coated with a hydrophilic polymer.

The implant injection tests are carried out with 27 D diopter implants and the outlet diameter of the cartridges/tips is 2 mm.

The results are summarized in Table 5 below.

TABLE 5

| No. | Nature of the cartridge/tip | Test carried out after 1 day of immersion | Test carried out after 7 days of immersion | Test carried out after 15 days of immersion | Test carried out after 30 days of immersion | Test carried out after 60 days of immersion |
|---|---|---|---|---|---|---|
| 6.1 | PP + hydrophilic coating | Low slipperiness | No slipperiness | No slipperiness | No slipperiness | No slipperiness |
| 6.2 | PP + 1% copolymer acrylate of Example 6 | Moderate slipperiness | Moderate slipperiness | Moderate slipperiness | Moderate slipperiness | Moderate slipperiness |
| 6.3 | PP + 2% copolymer acrylate of Example 6 | Moderate slipperiness | High slipperiness | High slipperiness | High slipperiness | High slipperiness |
| 6.4 | PP + 5% copolymer acrylate of Example 6 | Moderate slipperiness | High slipperiness | High slipperiness | High slipperiness | High slipperiness |

*Each test is carried out 3 times in order to validate the result obtained.
Low slipperiness: possibly leading to significant degradation of the implants (Applied force > 10N)
Moderate slipperiness: requiring a high force for the injection with the risk of alteration of the implants (5N < Applied force < 10N)
High slipperiness: allowing easy injection without risk of alteration of the implants (1N < Applied force < 5N)

The slipperiness is high for all the cartridges/tips manufactured from the metastable composition PA+copolymer of Example 3. The results are identical to those obtained with the hydrophilic implants.

EXAMPLE 13

The polyurethane copolymer of Example 6 with a molar mass of 25500 g/mol having two acrylate ends was compounded with the polypropylene PPR 10222 in an extruder at 240° C. in order to prepare the corresponding metastable compositions according to the protocol of Example 8. The compositions are stored at ambient temperature.

The utilization of the cartridge/tip is then carried out by injection/moulding of the corresponding metastable compositions in the presence of dicumyl peroxide (a radical initiator) at 220° C. The objective of the presence of the initiator is to allow the radical grafting of part of the functional copolymer chains by their acrylate ends to the polypropylene in order to create covalent bonds in the metastable composition. This makes it possible to have a hydrophilic surface which swells in the presence of water but does not solubilize. This characteristic makes it a device particularly suited to the systems using pre-loaded implants in a physiological liquid.

In order to validate the chemical grafting, the cartridges/tips are rinsed 5 times with water and ethanol, the chains not covalently bonded thus being removed. Raman microscopy analysis of the surface of the cartridge/tip shows the presence of the copolymer after the different washes.

The protocol adopted in order to characterize the properties of slipperiness is as follows: the polyhydroxyethylmethacrylate (PHEMA)-based hydrophilic implant is placed in the cartridge/tip then the physiological liquid is added and the pre-loaded device is stored at ambient temperature.

The results show that the slipperiness is high for cartridges/tips prepared from a metastable composition containing at least 2% of the copolymer comprising acrylate groups of Example 6. Unlike the PP-based reference system coated with a hydrophilic polymer the devices obtained from the metastable compositions exhibit identical behaviour after 2 months still with high slipperiness properties indicating that the functional copolymer is not leached out, nor solubilized by the physiological liquid.

The invention claimed is:

1. A metastable polymer composition consisting of a mixture of one constituent polymer and one functional copolymer, in which
said constituent polymer is a thermoplastic polymer having a glass transition temperature (Tg) or a melting temperature (Tm) above or equal to 80° C., and is present in the mixture in a mass proportion comprised between 85% and 99.9%, and
said functional copolymer has a glass transition temperature (Tg) or a melting temperature (Tm) above or equal to 40° C., comprises at least 60% by mass of monomer units with a hydrophilic character, and hydrophobic sequences or blocks, wherein said hydrophobic sequences or blocks are miscible with the constituent polymer and has a molecular weight greater that 5000 g/mole, wherein the molecular weight is expressed in average number.

2. The composition of claim 1, wherein the constituent polymer provides the material prepared from said mixture with mechanical properties and the functional copolymer provides said material with a character of slipperiness.

3. The composition of claim 1, wherein the constituent polymer is chosen from the polyolefins.

4. The composition of claim 1, wherein the functional copolymer has a glass transition temperature (Tg) below the Tg value of the constituent polymer or a melting temperature (Tm) below the Tm value of the constituent polymer.

5. The composition of claim 1, wherein the functional copolymer comprises between 60 and 99% by mass of hydrophilic monomer units.

6. The composition of claim 1, wherein the functional copolymer is chosen from random copolymers, block copolymers, comb copolymers and star copolymers.

7. The composition of claim 1, wherein the functional copolymer is chosen from the polyethers, polyesters and polyurethanes, wherein each of the polyethers, polyesters and polyurethanes have both hydrophilic and hydrophobic sequences or blocks, and copolymers based on (meth)acrylic acid, ethylene oxide, acrylamide, vinyl alcohol, vinyl pyrrolidone or hydroxyethyl(meth)acrylate combined with hydrophobic units partially miscible or compatible with the constituent polymer.

8. The composition of claim 1, wherein the functional copolymer moreover comprises reactive groups capable of reacting in the presence of free radicals in order to generate covalent bonds between the chains of the functional copolymer and the chains of the constituent polymer.

9. The composition of claim 1, wherein the composition is in a non-changing morphological state, at temperatures below the Tg/Tm of the different polymer components of the mixture and in that the composition is capable of changing towards a different multiphase morphological state at temperatures above the Tg/Tm of the polymer constituents.

10. A material prepared from a metastable composition according to claim 1.

11. A medical device part comprising
a metastable composition according to claim 1, which forms all or part of an ophthalmic implant injection device.

12. An ophthalmic implant injection device comprising at least one part prepared from a metastable composition according to claim 1.

13. Method for manufacturing a material, a medical device part or a medical device, comprising:
introducing a mixture of at least one constituent polymer and at least one partially miscible or compatible functional copolymer as defined in claim 1 in an extruder;
recovering a metastable polymer composition as defined in claim 1;
processing the metastable polymer composition by injection molding; and
recovering a medical device part or a medical device formed from the metastable polymer composition.

14. The method of claim 13, wherein said medical device is an ophthalmic implant injection device.

* * * * *